United States Patent [19]

Murase et al.

[11] Patent Number: 5,780,710
[45] Date of Patent: Jul. 14, 1998

[54] GAS ANALYZER AND METHOD OF CALIBRATING SAID GAS ANALYZER

[75] Inventors: Takao Murase, Konan; Jun Usami, Nukata-gun; Masao Kon, Nagoya, all of Japan

[73] Assignee: NGK Insulators, Ltd., Japan

[21] Appl. No.: 863,617

[22] Filed: May 27, 1997

[30] Foreign Application Priority Data

May 30, 1996 [JP] Japan ................ 8-136610
Apr. 23, 1997 [JP] Japan ................ 9-106167

[51] Int. Cl.$^6$ ................ G01N 27/409
[52] U.S. Cl. ................ 73/1.06; 205/781
[58] Field of Search ................ 73/1.06, 1.07, 73/23.31; 204/426, 427; 205/781, 784; 422/94, 98

[56] References Cited

U.S. PATENT DOCUMENTS 4,981,125  1/1991  Kato et al. ................ 205/784
5,397,442  3/1995  Wachsman ................ 73/23.31

FOREIGN PATENT DOCUMENTS

| 0 678 740 A1 | 10/1995 | European Pat. Off. |
| 406160325 | 6/1984 | Japan ................ 73/23.31 |
| 63-38154 | 2/1988 | Japan . |
| 64-39545 | 2/1989 | Japan . |
| 1-277751 | 11/1989 | Japan . |
| 2-1543 | 1/1990 | Japan . |

Primary Examiner—Robert Raevis
Attorney, Agent, or Firm—Parkhurst & Wendel

[57] ABSTRACT

A gas analyzer includes a gas sensor, a drive section that pumps oxygen in first to third processing zones of the gas sensor, an operating section that operates a pumping current flowing in a third electro-chemical pump cell into a gas value to be measured, a display output section that displays a value operated by the operating section, or outputs the value as an electrical output to the external, and a heater drive section that heats the gas sensor to a predetermined temperature.

11 Claims, 8 Drawing Sheets

GAS ANALYZER AND METHOD OF CALIBRATING SAID GAS ANALYZER

BACKGROUND OF THE INVENTION

1. Field of the Invention

The present invention relates to a gas analyzer that measures a gas component to be measured such as $NO_x$, which has bound oxygen, and a method of calibrating the gas analyzer.

2. Description of Related Art

Up to now, in order to find the concentration of a desired gas component contained in a gas to be measured, there has been proposed a variety of measuring methods and devices. For example, there has been known, as a method of measuring $NO_x$ in a gas to be measured such as a combustion gas, a technique in which a sensor that is made up of a Pt electrode and an Rh electrode being formed on a solid electrolyte of oxygen ion conduction such as zirconium using the $NO_x$ reduction property of Rh is used to measure the electromotive force between those two electrodes. However, in the sensor of this type, its electromotive force not only changes largely with respect to a change in the concentration of oxygen contained in a combustion gas which is a gas to be measured, but also changes mildly with respect to a change in the concentration of $NO_x$. As a result, such a sensor is liable to be adversely affected by noises.

Also, in order to exhibit the reduction property of $NO_x$, a reducing gas such as CO is essential. For that reason, there has arisen such a defect that since the generated amount of CO is lower than the generated amount of $NO_x$ under the combustion condition where a fuel is excessively reduced under which a large amount of $NO_x$ is generally generated, the combustion gas produced under such a combustion condition cannot be measured.

Also, there has been known from Japanese Patent Application Laid-Open No. 63-38154, Japanese Patent Application Laid-Open No. 64-39545 and so on, a system in which one set of electro-chemical pump cell and sensor cell which are made up of a Pt electrode and a solid electrolyte of the oxygen ion conduction are combined with another set of electro-chemical pump cell and sensor cell which are made up of an Rh electrode and a solid electrolyte of the oxygen ion conduction, so that $NO_x$ is measured in accordance with a difference between the current values of the respective pumps.

Further, there has been proposed in Japanese Patent Application Laid-Open No. 1-277751, Japanese Patent Application Laid-Open No. 2-1543, and so on, a method in which two sets of electro-chemical pump cells and sensor cells are prepared, and a sensor made up of one set of the pump cell and sensor cell measures a limit pump current under an oxygen partial pressure where $NO_x$ is not reduced, and another sensor made up of the other set of the pump cell and sensor cell measures a limit pump current under an oxygen partial pressure where $NO_x$ is reduced, to thereby obtain a difference between those limit pump currents, or in which a sensor made up of a set of pump cell and sensor cell is used, and an oxygen partial pressure in a gas to be measured is switched to an oxygen partial pressure where $NO_x$ is reduced and an oxygen partial pressure where $NO_x$ is not reduced, to thereby measure a difference between the limit currents.

However, in the above-mentioned $NO_x$ measuring system, a value of the limit current is normally occupied mainly by the current based on a large amount of oxygen contained in the gas, and a target current based on $NO_x$ is extremely small, with the result that a small current value corresponding to $NO_x$ is obtained by a large difference between those two current values. For that reason, in the case of measuring the difference by switching a set of sensors, there arises such a problem that continuous measurement cannot be performed, the response or accuracy is deteriorated, or the like. Also, in the case of using two sets of sensors, when the concentration of oxygen in the gas to be measured is largely changed, an error is liable to occur in the measured value. Thus, the system using two sets of sensors cannot be used in the case where the concentration of oxygen in the gas to be measured is largely changed. This is because the dependency of the pump current of one sensor on the concentration of oxygen is different from the dependency of the pump current of the other sensor on the concentration of oxygen.

Further, there arises a defect that when a difference occurs in the aging change of the characteristics of two sets of sensors, the difference becomes an error as it is, so that the system cannot be used for a long time.

As described above, oxygen existing in the gas to be measured causes such a problem that an accuracy of measurement is deteriorated in measuring $NO_x$ or other gas components to be measured, etc.

Under the above circumstances, in order to solve the above problems, the present inventors have proposed in European Patent Publication 0678740 A1, a measuring method which is capable of measuring a gas component to be measured having bound oxygen such as $NO_x$ or the like in the gas to be measured, using first and second electro-chemical pump cells which are disposed in series, without being adversely affected by the concentration of oxygen in the gas to be measured or by a change of that concentration, with an excellent continuous response, and with an accuracy for a long time.

This novel measuring method is carried out as follows: a gas to be measured which contains a gas component to be measured having bound oxygen to be measured is sequentially introduced from an external space where a gas to be measured exists into first and second processing zones under the respective predetermined diffused resistances; and firstly in the first processing zone, oxygen in an atmosphere is controlled to a predetermined oxygen partial pressure by the first electro-chemical pump cell; in the second processing zone, oxygen is controlled to a low oxygen partial pressure value that does not substantially influence the measurement of the amount of said gas component to be measured, while in a third processing zone, the gas component to be measured in the atmosphere introduced from said second processing zone is reduced or decomposed; and oxygen generating at that time is pumped out due to the pumping action of oxygen using the third electro-chemical pump cell, to thereby detect the pump current that flows in the third electro-chemical pump cell so that the amount of the gas component to be measured in the gas to be measured is obtained according to its detection value.

SUMMARY OF THE INVENTION

The present invention has been made to further improve the above-mentioned measuring method, and therefore an object of the present invention is to provide a gas analyzer and a method of calibrating an analyzed value, which are capable of making measurement with an excellent continuous response, with an accuracy for a long time and without being adversely affected by the increased concentration of oxygen in the gas to be measured, and also are capable of obtaining a high S/N ratio, and obtaining a large change in signals even in measurement of a gas component to be measured having a low concentration.

In order to achieve the above object, according to the present invention, there is provided a gas analyzer comprising: a gas sensor in which after a gas to be measured containing a gas component to be measured having bound oxygen to be measured is introduced into a first processing zone under a predetermined diffusion resistance, and an oxygen partial pressure in the atmosphere within said first processing zone is controlled to a predetermined oxygen partial pressure due to the pumping action of oxygen by the first electro-chemical pump cell in said first processing zone, the gas to be measured is introduced into a second processing zone under a predetermined diffusion resistance, and oxygen is pumped out by the second electro-chemical pump cell in the second processing zone, so that the oxygen partial pressure in said atmosphere is controlled to a low oxygen partial pressure value that does not substantially influence the measurement of the amount of the gas component to be measured, and thereafter the gas to be measured is introduced into a third processing zone, and said gas component to be measured in the atmosphere introduced from said second processing zone is reduced or decomposed in said third processing zone, and oxygen generating at that time is pumped out by a third electro-chemical pump cell to detect a pumping current flowing in said third electro-chemical pump cell;

a drive section for pumping oxygen from said first to third processing zones in said gas sensor;

an operating section for operating the pumping current flowing in said third electro-chemical pump cell into a value of the gas to be measured;

a display output section for displaying the value operated by said operating section, or outputting the value to an external as an electric output; and a heater drive section for heating said gas sensor to a predetermined temperature.

In the present invention, it is preferable that the pumping current in the first processing zone and the pumping current in the second processing zone are introduced into the operating section, and the operating section operates the pumping currents in the first and second processing zones to output the amount of oxygen, the amount of insufficient oxygen or its equivalent in the atmosphere to be measured.

Also, it is preferable that the gas component to be measured is $NO_x$, and the measured $NO_x$ is corrected according to the amount value of oxygen, the amount value of insufficient oxygen or an equivalent value of oxygen measured.

Further, it is preferable that at least the drive section is formed integrally with said gas sensor.

Furthermore, according to the present invention, there is provided a method of calibrating a gas analyzer which includes a gas sensor in which after a gas to be measured containing a gas component to be measured having bound oxygen to be measured is introduced into a first processing zone under a predetermined diffusion resistance, and an oxygen partial pressure in the atmosphere within said first processing zone is controlled to a predetermined oxygen partial pressure due to the pumping action of oxygen by the first electro-chemical pump cell in said first processing zone, the gas to be measured is introduced into a second processing zone under a predetermined diffusion resistance, and oxygen is pumped out by the second electro-chemical pump cell in the second processing zone, so that the oxygen partial pressure in said atmosphere is controlled to a low oxygen partial pressure value that does not substantially influence the measurement of the amount of the gas component to be measured, and thereafter the gas to be measured is introduced into a third processing zone, and said gas component to be measured in the atmosphere introduced from said second processing zone is reduced or decomposed in said third processing zone, and oxygen generating at that time is pumped out by a third electro-chemical pump cell to detect a pumping current flowing in said third electro-chemical pump cell; said method of comprising the step:

calibrating said gas analyzer with a plurality of known gas component to be measured as a standard gas and a pumping current corresponding to the standard gas as a calibration curve.

In the present invention, it is preferable that the standard gas containing at least $H_2O$ and $CO_2$ is used as the known gas component to be measured other than the gas component to be measured.

Also, it is preferable that a temperature of said gas sensor is increased 50° C. higher than a working temperature for a predetermined time before measuring the calibration curve, the temperature of said gas sensor is returned to the working temperature to prepare the calibration curve of the standard gas.

Further, it is preferable that before measuring the calibration curve, said gas sensor is separated from said drive section, and an alternating current power supply is connected between the respective electrode pair of said first to third processing zones, and after an alternating current of 1 Hz or higher is supplied for a predetermined time, said gas sensor is returned to a drive state to prepare the calibration curve of the standard gas.

BRIEF DESCRIPTION OF THE DRAWINGS

The above and other objects and features of the present invention will be more apparent from the following description taken in conjunction with the accompanying drawings.

FIGS. 3A and 3B are structural diagrams showing an example of an $NO_x$ sensor which is a structural element that constitutes a gas analyzer of the present invention, in which FIG. 3A is an explanatory plan view showing the $NO_x$ sensor, and FIG. 3B is an explanatory enlarged diagram showing a main portion of the $NO_x$ sensor taken along a line III—III of FIG. 3A;

DETAILED DESCRIPTION OF THE PREFERRED EMBODIMENTS

Now, a description will be given in more detail and specifically of a gas analyzer in accordance with the present invention with reference to the accompanying drawings.

First, a description will be given in more detail of a gas sensor which is a structural element that constitutes a gas analyzer in accordance with the present invention.

Figure 3:
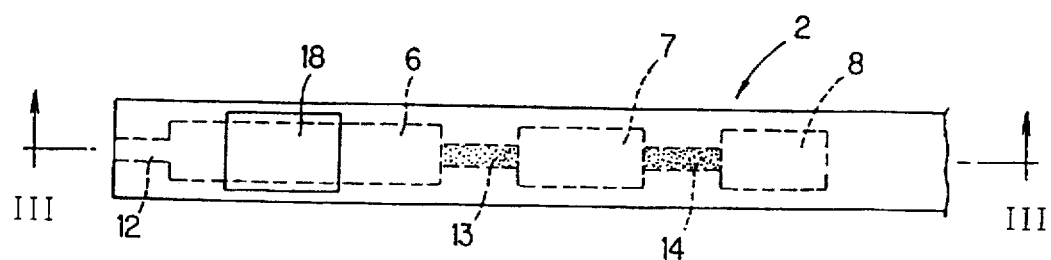
Figure 3:
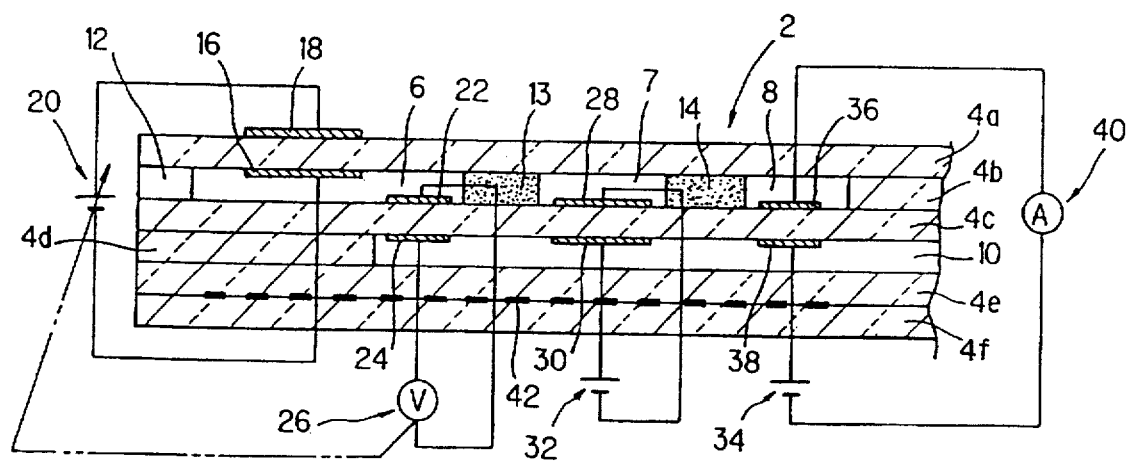

FIGS. 3A and 3B are structural diagrams showing an example of an $NO_x$ sensor which is a structural element that constitutes a gas analyzer of the present invention, in which FIG. 3A is an explanatory plan view showing the $NO_x$ sensor, and FIG. 3B is an explanatory enlarged diagram showing a main portion of the $NO_x$ sensor taken along a line III—III of FIG. 3A.

As shown in FIGS. 3A and 3B, reference numeral 2 denotes a sensor device which is in the form of an elongated slender plate-like body, and as is apparent from FIG. 3B, the sensor device 2 is formed of a plate body having an integral structure in which a plurality of solid electrolyte layers 4a, 4b, 4c, 4d, 4e and 4f of the ion conduction which are fine and air-tight are laminated. The respective solid electrolyte layers 4a to 4f are made of a known solid electrolyte material of the oxygen ion conduction such as zirconium porcelain. Then, the sensor device 2 of the integral structure is manufactured by integrally sintering a laminate of non-sintered solid electrolyte as in the conventional manner.

Then, within the above sensor device 2 of the integral structure, a first inner space 6, a second inner space 7 and a third inner space 8 which are in the form of a rectangular plane, respectively, are disposed in such a manner that the respective spaces are sectioned from the external, respectively, so that the first inner space 6 is positioned at a tip side of the device, and the third inner space 8 is positioned on a base end side of the device, to thereby form a first processing zone, a second processing zone and a third processing zone. Also, a reference air introduction passage 10 as a reference gas existent space is disposed to extend along the longitudinal direction of the sensor device 2 in such a manner that it is independent from the first, second and third inner spaces 6, 7 and 8 and superimposed vertically on each other. The reference air introduction passage 10 is designed to open at an end portion of the base side of the sensor device 2 so that it communicates with the air. In this example, the first, second and third inner spaces 6, 7 and 8 are formed in a state that they are positioned on substantially the same plane with the structure that spaces corresponding to the first, second and third inner spaces 6, 7 and 8 formed in the solid electrolyte 4b are covered with upper and lower solid electrolyte layers 4a and 4c. The reference air introduction passage 10 is formed such that a space corresponding to the reference air introduction passage 10 formed in the solid electrolyte layer 4d is covered with the solid electrolytes 4c and 4e from the upper and the lower, respectively.

Also, a first diffusion rate-limiting passage 12 which is a first diffusion rate-limiting means that allows the first inner space 6 to communicate with the external space in which the gas to be measured exists is formed by notching the solid electrolyte 4b so that it opens at the tip of the sensor device 2. Through the first diffusion rate-limiting passage 12, the gas to be measured which contains $NO_x$ as the gas component to be measured is introduced into the first inner space 6 under a predetermined diffusion resistance.

Likewise, an annular notch is defined in a part of the solid electrolyte layer 4b positioned between the first inner space 6 and the second inner space 7, and in a part of the solid electrolyte layer 4b positioned between the second inner space 7 and the third inner space 8, respectively, to thereby form second and third diffusion rate-limiting passages 13 and 14 that constitute second and third rate-limiting means, respectively.

Those second and third diffusion rate-limiting passages 13 and 14 are filled with a porous member made of alumina or the like, respectively, so that the diffusion resistances of those passages 13 and 14 are set to be larger than the diffusion resistance of the first diffusion rate-limiting passage 12. Then, through the second diffusion rate-limiting passage 13, the atmosphere within the first inner space 6 is introduced into the second inner space 7 under a predetermined diffusion resistance, and also the atmosphere within the second inner space 7 is introduced into the third inner space 8 under a predetermined diffusion resistance.

A part of the solid electrolyte film 4a which is exposed to the first inner space 6 is provided with a first inside pump electrode 16 which is in contact with that part of the solid electrolyte film 4a and formed of a rectangular porous cermet electrode, and an outer surface of the solid electrolyte layer 4a corresponding to the first inside pump electrode 16 is provided with a first outer pump electrode 18 which is in contact with the outer surface of the solid electrolyte layer 4a and formed of the same rectangular porous cermet electrode, whereby those electrodes 16, 18 and the solid electrolyte layer 4a constitute a first electro-chemical pump cell.

Then, a desired voltage is applied between those two electrodes 16 and 18 of the first electro-chemical pump cell by an external variable power supply 20 so that a current flows from the first outside pump electrode 18 toward the first inside pump electrode 16, thereby being capable of pumping out oxygen in the atmosphere within the first inner space 6 to the space in which the gas to be measured exists. If the current flows in an opposite direction, oxygen is pumped in the first inner space 6 from the external space in which the gas to be measured exists. The porous cermet electrode is made of metal such as Pt and ceramics such as $ZrO_2$, and the first inside pump electrode 16 disposed within the first inner space 6 which is in contact with the gas to be measured needs to be made of a metal which is weak in the reduction of the $NO_x$ component in the gas to be measured or has no reduction of the $NO_x$ component therein. For example, it is preferable that the first inside pump electrode 16 is made of a cermet consisting of Pt-Au alloy and $ZrO_2$.

Further, a part of the solid electrolyte layer 4c which is exposed to the first inner space 6 is provided with a measurement electrode 22 which is in contact with that part of the solid electrolyte layer 4c and formed of a porous cermet electrode like the first inside pump electrode 16, and a part of the solid electrolyte layer 4c which is exposed to the reference air introduction passage 10 is provided with a reference electrode 24 which is in contact with that part of the solid electrolyte layer 4c and formed of a porous cermet electrode like the first outside pump electrode 18, whereby the measurement electrode 22, the reference electrode 24 and the solid electrolyte layer 4c constitute an electro-chemical cell as an oxygen partial pressure detecting means, that is, an electro-chemical sensor cell. As well known, an electromotive force developed between the measurement electrode 22 and the reference electrode 24 is measured by a potentiometer 26 on the basis of a difference in the concentration of oxygen between the atmosphere within the first inner space 6 and a reference air (atmosphere) within the reference air introduction passage 10, to thereby detect a partial pressure of oxygen in the atmosphere within the first inner space 6. Then, the voltage applied from the variable power supply 20 is controlled on the basis of a value of the partial pressure of oxygen in the atmosphere within the first inner space 6 which has been detected by the potentiometer 26, whereby the pumping action of the first electro-chemical pump cell is controlled in such a manner that the partial pressure of oxygen in the atmosphere within the first inner space 6 becomes a predetermined value which is sufficiently low to the degree that the partial pressure of oxygen can be controlled in the succeeding second inner space 7.

On the other hand, a second inside pump electrode 28 formed of a porous cermet electrode like the first inside pump electrode 16 is provided on the solid electrolyte layer 4c in such a manner that it is positioned within the second inner space 7 and is in contact with the solid electrolyte layer 4c. Also, a part of the solid electrolyte layer 4c corresponding to the inside pump electrode 28 which is exposed to the reference air introduction passage 10 is provided with a second outside pump electrode 30 formed of a porous cermet electrode like the first outside pump electrode 18, and the inside pump electrode 28, the outside pump electrode 30 and the solid electrolyte layer 4c constitute a second electro-chemical pump cell. A desired voltage is applied between those two electrodes 28 and 30 of the second electro-chemical pump cell by an external d.c. power supply 32 so that a current flows from the second outside pump electrode 30 side to the second inside pump electrode 28 side, with the result that a partial pressure of oxygen in the atmosphere within the second inner space 7 is controlled to a low partial pressure of oxygen which does not substantially adversely affect the measurement of the amount of the gas component to be measured, in a situation where the gas component ($NO_x$) to be measured cannot be substantially reduced or decomposed.

Further, a rectangular third inside pump electrode 36 is disposed on a part of the solid electrolyte layer 4c which is exposed to the third inner space 8 within the third inner space 8 in such a manner that the third inside pump electrode 36 is in contact with that part of the solid electrolyte layer 4c. The third inside pump electrode 36 is made of a porous cermet consisting of Rh which is a metal that can reduce $NO_x$ which is the gas component to be measured and $ZrO_2$ as ceramics, whereby the electrode 36 functions as an $NO_x$ reduction catalyst that can reduce $NO_x$ existing in the atmosphere within the third inner space 8. In addition, a constant voltage is applied between the third inside pump electrode 36 and a third outside pump electrode 38 disposed within the reference air introduction passage 10 in correspondence with the third inside pump electrode 36, whereby oxygen in the atmosphere within the third inner space 8 is pumped out within the reference air introduction passage 10.

With the above structure, in this example, a third electro-chemical pump cell is made up of the third inside pump electrode 36, the third outside pump electrode 38 and the solid electrolyte layer 4c. Then, a pumping current flowing due to the pumping action of the electro-chemical pump cell is detected by an ammeter 40. It should be noted that the above-mentioned constant voltage (d.c.) power supply 34 is designed such that a voltage having a magnitude that gives a limit current to the pumping of oxygen produced when $NO_x$ is decomposed in the third electro-chemical pump cell can be applied under the condition where limited $NO_x$ flows in the third diffusion rate-limiting passage 14.

A plurality of heaters 42 which are allowed to heat by the supply of electricity from the external are embedded within the sensor device 2 in such a manner that the heaters 42 are interposed between the solid electrolyte layers 4e and 4f from the upper and the lower, respectively. On the upper and lower surfaces of the heaters 42, a ceramic thin layer made of alumina, etc., although being not shown is formed to obtain electrical insulation between the heater 42 and the solid electrolyte layers 4e, 4f, respectively. The heaters 42, as shown in FIG. 3B, are disposed over the entire portions of from the first inner space 6 to the third inner space 8, whereby those inner spaces 6, 7 and 8 are heated to a predetermined temperature, respectively, in such a manner that not only the first, second and third electro-chemical pump cells but also the electro-chemical sensor cell are heated and held to a predetermined temperature, respectively.

Therefore, in the sensor device 2 thus structured, its tip side is disposed within the space in which the gas to be measured exists, whereby the gas to be measured is led to the first inner space 6 through the first diffusion rate-limiting passage 12 defined in the sensor device 2 under a predetermined diffusion resistance. Then, the gas to be measured which has been led to the first inner space 6 is subjected to the pumping action of oxygen developed by applying a predetermined voltage between the two electrodes 16 and 18 that constitute the first electro-chemical pump cell so that a partial pressure of oxygen is controlled to a predetermined value.

It should be noted that in order to set the partial pressure of oxygen in the atmosphere within the first inner space 6 to the predetermined value, there is applied a technique in which an electromotive force exerted between the measurement electrode 22 and the reference electrode 24 in the electro-chemical sensor cell is measured by the potentiometer 26 on the basis of the well-known Nernst's equation, to control a voltage (variable voltage 20) which is applied between the two electrodes 16 and 18 of the first electro-chemical pump cell.

In other words, a voltage of the first electro-chemical pump cell is controlled so that the electromotive force corresponds to a difference between a predetermined concentration of oxygen in the first inner space 6 and the concentration of oxygen in the reference air. In this example, the first diffusion rate-limiting passage 12 functions to restrict, when a voltage is applied to the first electro-chemical pump cell, the amount of oxygen in the gas to be measured which flows in the space to be measured (first inner space 6) in a diffused manner, to thereby restrain a current flowing in the first electro-chemical pump cell.

In the case where the concentration of oxygen in the gas to be measured is equal to or higher than a predetermined value, oxygen is pumped out by the pumping action of oxygen of the first electro-chemical pump cell, but in the case where the concentration of oxygen in the gas to be measured is lower than the predetermined value or zero, oxygen is pumped in from the external space by the pumping action of oxygen of the first electro-chemical pump cell, so that the partial pressure of oxygen in the atmosphere within the first processing zone is controlled to the predetermined partial pressure of oxygen.

Also, within the first inner space 6, even under the circumstances where heating is made by the external gas to be measured, and further by the heater 42, a state of the partial pressure of oxygen where $NO_x$ in the atmosphere is not reduced by the inside pump electrode 16 or the measurement electrode 22, for example, a state of the partial pressure of oxygen where the reaction of $NO \rightarrow 1/2N_2 + 1/2O_2$ does not occur is given. This is because if $NO_x$ in the gas to be measured (atmosphere) is reduced within the first inner space 6, $NO_x$ cannot be accurately measured in the succeeding third inner space 8. From this viewpoint, it is necessary that a state in which $NO_x$ cannot be reduced by a component related to the reduction of $NO_x$ (in this example, a metal component of the inside pump electrode 16 and the measurement electrode 22) is given within the first inner space 6.

For the above reason, the second electrochemical pump cells (4c, 28, 30) are provided in the second inner space 7 so that the partial pressure of oxygen in the atmosphere within the second inner space 7 can be always held to a constant low partial pressure value of oxygen, whereby even though the partial pressure of oxygen in the atmosphere which can be introduced from the first inner space 6 by the pumping action is changed depending on the concentration of oxygen in the gas to be measured, the partial pressure of oxygen in the atmosphere within the second inner space 7 can be always held constant low value. As a result, the partial pressure of oxygen can be controlled to a low partial pressure value of oxygen which does not substantially adversely affect the measurement of $NO_x$.

Similarly, within the second inner space 7, there is given a state of the partial pressure of oxygen where $NO_x$ in the atmosphere is not reduced under the circumstances in which heating is made by the external gas to be measured or by the heater 24 by the second inside pump electrode 28, as in the first inner space 6. For that reason, likely to the first inside pump electrode 16 and the measurement electrode 22, the second inside pump electrode 28 is made of an electrode material which has no reduction with respect to the gas to be measured, or is low in reduction.

With the above structure, the gas to be measured in which a partial pressure of oxygen is controlled within the second inner space 7 is led to the third inner space 8 through the third diffusion rate-limiting passage 14 under a predetermined diffusion resistance. Then, the gas to be measured which has been introduced into the third inner space 8 is subjected to the pumping action of oxygen by applying a predetermined voltage between the third inside pump electrode 36 and the third outside pump electrode 38 which constitute the third electro-chemical pump cell in a direction in which oxygen is pumped out from the third inner space 8 toward the reference air introduction passage 10 side, with the results that the concentration of oxygen is further lowered, in particular, on a three-phase interface of the third inside pump electrode 36, in the third inner space 8, and $NO_x$ is controlled to a reduced state in the periphery of the inside pump electrode 36 that also functions as the reduction catalyst. In this situation, a current that flows in the third electro-chemical pump becomes a value proportional to the concentration of oxygen in the atmosphere which is led to the third inner space 8, that is, a sum of the concentration of oxygen in the atmosphere within the second inner space 7 and the concentration of oxygen generated by making $NO_x$ reduced by the third inside pump electrode 36. However, since the concentration of oxygen in the atmosphere within the second inner space 7 is controlled to be held constant by the second electro-chemical pump cell, a current flowing in the third electro-chemical pump cell is proportional to the concentration of $NO_x$. Then, the concentration of $NO_x$ corresponds to the amount of diffusion of $NO_x$ which is limited by the third diffusion rate-limiting passage 14, thus being capable of measuring the concentration of $NO_x$.

Figure 4:
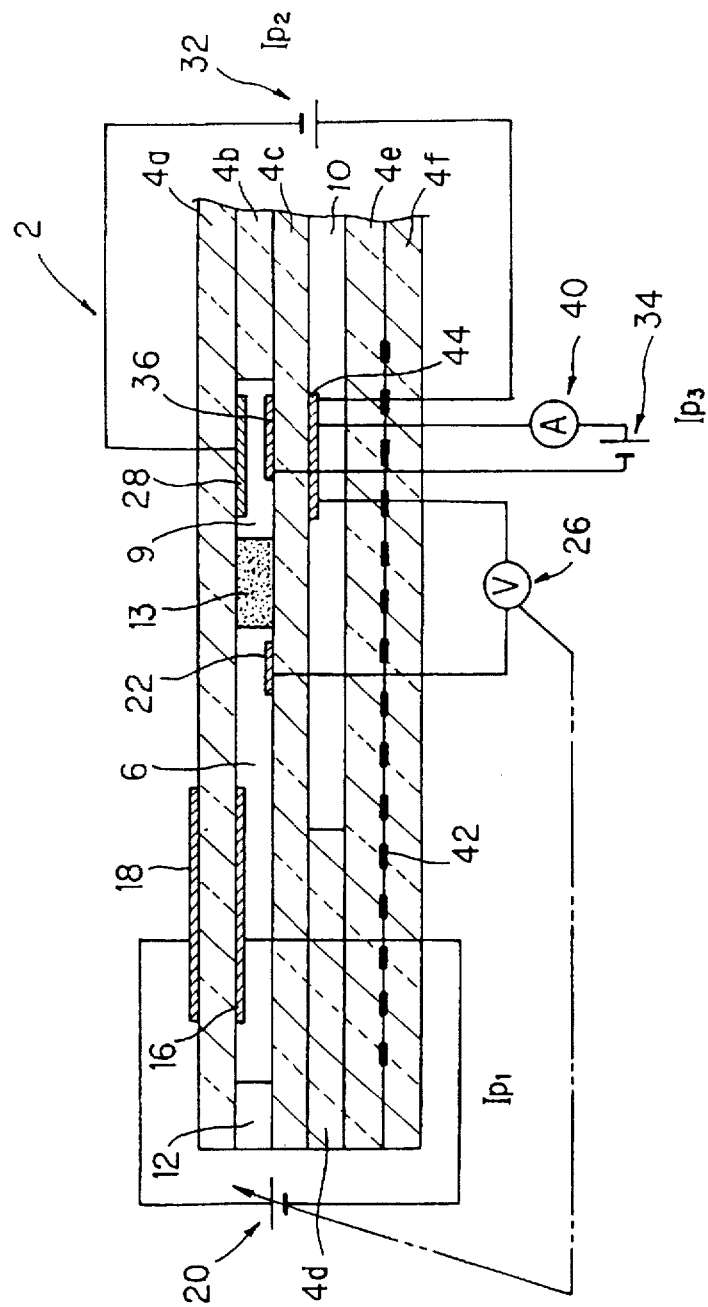
FIG. 4 is a cross-sectional view showing a modified example of the $NO_x$ sensor which is a structural element that constitutes a gas analyzer of the present invention.

FIG. 4 is a cross-sectional view showing a modified example of the $NO_x$ sensor which is a structural element that constitutes a gas analyzer of the present invention.

In the modified example shown in FIG. 4, unlike the example shown in FIGS. 3A and 3B, the second inner space 7 and the third inner space 8 are integrated with each other to form an integral inner space 9 consisting of one small flat space in which the second inside pump electrode 28 and the third inside pump electrode 36 are disposed. Also, this modified example is characterized in that the reference electrode 24 of the electro-chemical sensor cell disposed within the reference air introduction passage 10, the second outside pump electrode 30 in the second electro-chemical pump cell, and the third outside pump electrode 38 in the third electro-chemical pump cell are structured by one common electrode 44.

In this modified example, the integral inner space 9 is structured with the second processing zone and the third processing zone, and the gas to be measured which has been introduced from the first inner space 6 through the second diffusion rate-limiting passage 13 is subjected to the pumping action of oxygen due to the second electro-chemical pump cell which is made up of the second inside pump electrode 28 and the second outside pump electrode 30 disposed on the intake side of the integral inner space 9 and the solid electrolyte layers 4a, 4b and 4c, whereby the gas to be measured is controlled to a constant low value of the partial pressure of oxygen, and is diffused under a predetermined diffusion resistance which is regulated by the small flat space of the integral inner space 9 to reach the third electrochemical pump cell disposed on the back side of the integral inner space 9, where $NO_x$ which is the gas component to be measured is reduced by the third inside pump electrode 36. Also, oxygen is pumped out from the third inside pump electrode 36 to the third outside pump electrode 38, to thereby detect the pumping current of the third electro-chemical pump cell by the ammeter 40.

Subsequently, a gas analyzer including the above-mentioned gas sensor therein in accordance with the present invention will be described.

Figure 1:
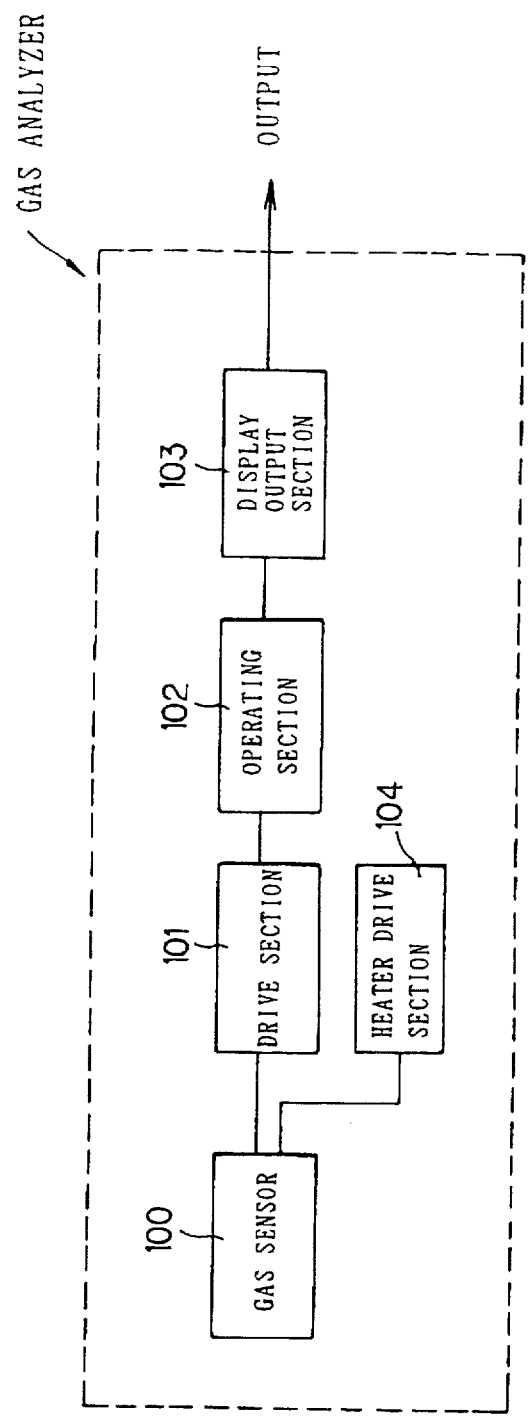
FIG. 1 is a block diagram showing an example of the structure of a gas analyzer in accordance with the present invention.

FIG. 1 is a block diagram showing an example of the structure of a gas analyzer in accordance with the present invention. The gas analyzer according to the present invention fundamentally includes a gas sensor 100, a drive section 101 that pumps oxygen from the gas sensor 100, an operating section 102 that operates a pumping current flowing in the electro-chemical pump cell of the gas sensor 100 into a gas value to be measured, a display output section 103 that displays a value operated by the operating section 102, or outputs the value as an electrical output to the external, and a heater drive section 104 that heats the gas sensor 100 to a predetermined temperature.

In this example, the operating section 102 has a function to operate the pumping current flowing in the third electro-chemical pump cell into the gas value to be measured. Preferably, the operating section 102 further inputs the pumping current (lp1) in the first processing zone and the pumping current (lp2) in the second processing zone to operate and output the amount of oxygen or the amount of insufficient oxygen in the gas to be measured or an equivalent thereof. As an equivalent of a gas to be measured is specifically a coefficient of excess oxygen (value of λ) or an air-fuel ratio (A/F value). This can be obtained on the basis of the fact that (A*lp1+B*lp2+C*lp3) is proportional to the total amount of oxygen in the gas to be measured. It should be noted that A, B and C are constants, respectively, and lp3 is the pumping current flowing in the third electro-chemical pump cell, that is, the pumping current in the third processing zone.

Figure 6:
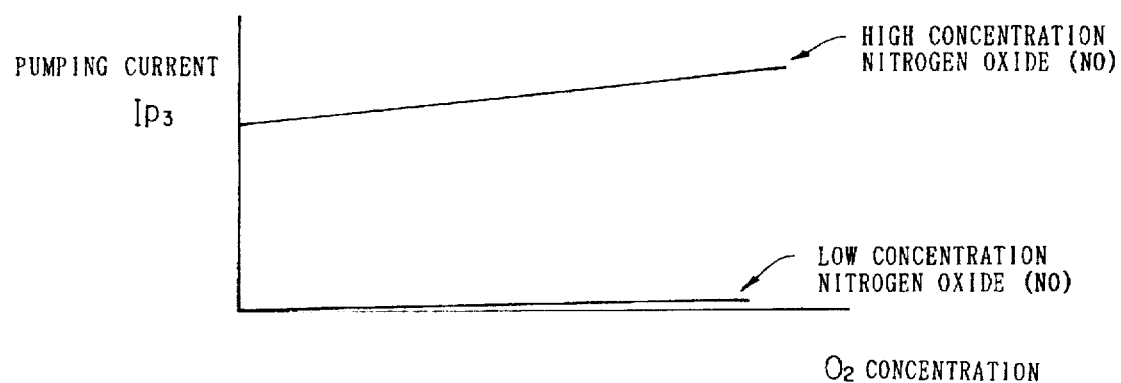
FIG. 6 is a graph showing a relationship between the concentration of oxygen in a gas to be measured and a pumping current (lp3)

In the present invention, a $NO_x$ concentration in a gas to be measured is preferably adjusted or corrected depending on an oxygen amount in a gas to be measured, an insufficient oxygen amount, or an equivalent. In this case, a value obtained by a calculation on the basis of (Ip1+Ip2+Ip3) as the oxygen amount, the insufficient oxygen amount, or the equivalent (coefficient of excess oxygen, air-fuel ratio, or the like) is preferably used for adjusting a $NO_x$ concentration. Alternatively, a value obtained by a calculation on the basis of (Ip1) or (Ip1+Ip2) may be used to make the calculation simpler. For example, the pumping current (Ip3) in the third processing zone depends upon the concentration of oxygen in the gas to be measured. As shown in FIG. 6, in the case where the concentration of $NO_x$ in the gas to be measured is high, the pumping current slightly fluctuates depending on the concentration of oxygen in the gas to be measured. From this viewpoint, it is preferable that the dependency of the pumping current (Ip3) on the concentration of oxygen in the gas to be measured is measured, and the measured data is stored in the operating section 102 in advance so that the concentration of $NO_x$ in the gas to be measured is corrected.

Incidentally, though an adjustment or correction concerning an oxygen reliability is explained as one example in FIG. 6, it is possible to adjust a reliability of $NO_x$ concentration value in a reducing gas, a neutral gas, or an oxidizing gas if the axis of abscissas expresses an equivalent (coefficient of excess oxygen, air-fuel ratio, or the like) as another example.

Figure 2:
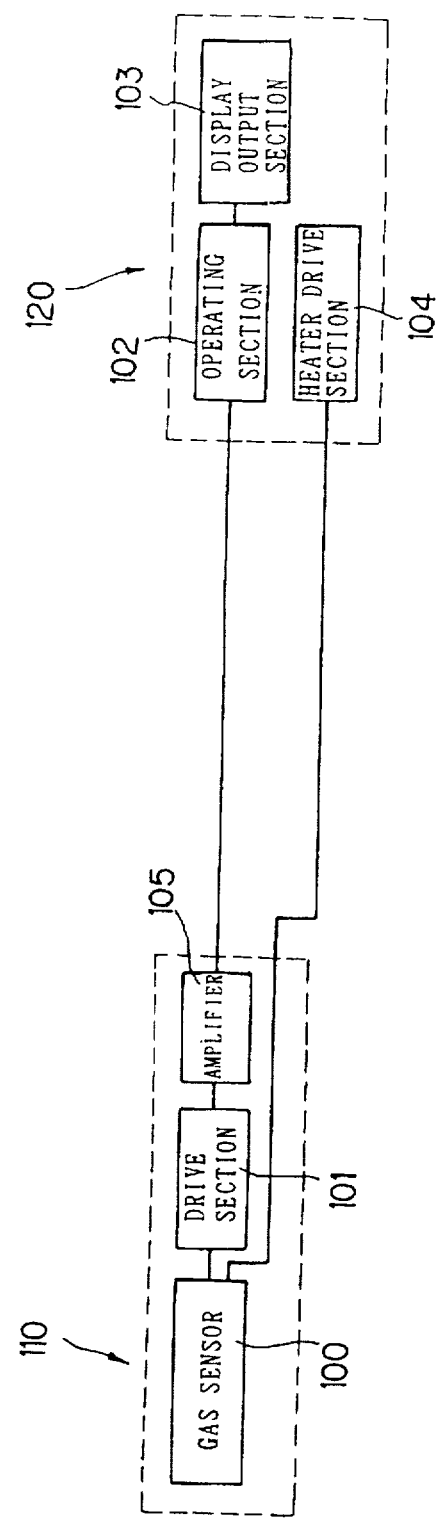
FIG. 2 is a block diagram showing another example of the structure of a gas analyzer in accordance with the present invention.

FIG. 2 is a block diagram showing another example of the structure of a gas analyzer in accordance with the present invention. In the gas analyzer shown in FIG. 2, a gas sensor is apart from a receiver unit such as an operating section. A gas sensor 100, a drive section 101 that pumps oxygen from the gas sensor 100, and an amplifier 105 that amplifies the pumping current obtained by the drive section 101 are integrated into a sensor probe 110, and at a position apart from the sensor probe 110, a receiver unit 120 which is made up of an operating section 102, a display output section 103 and a heater drive section 104 is disposed.

Figure 5:
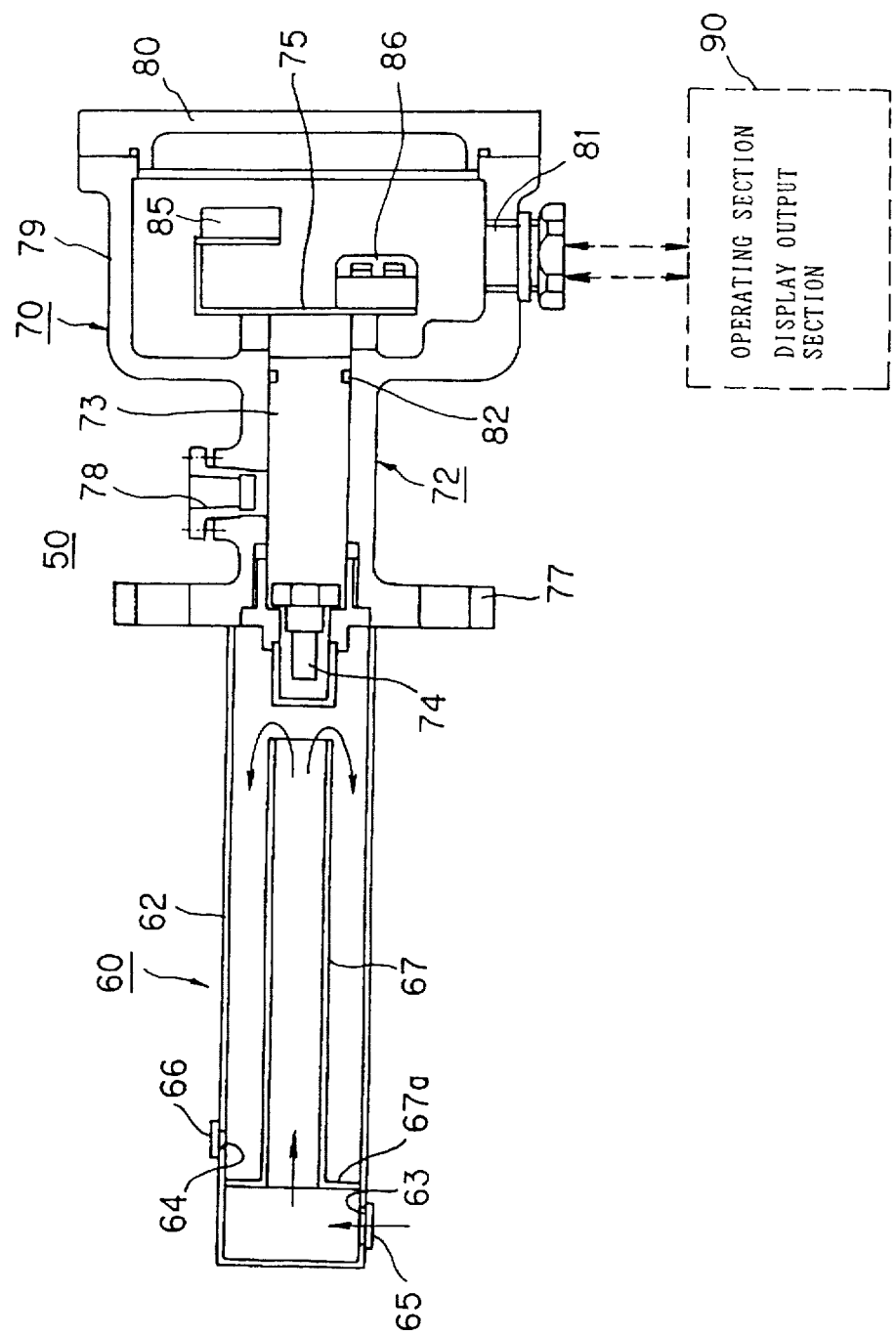
FIG. 5 shows a specific gas analyzer of the gas analyzer shown in the block diagram of FIG. 2.

FIG. 5 shows a specific gas analyzer of the gas analyzer shown in the block diagram of FIG. 2.

In FIG. 5, a gas analyzer 50 is made up of a gas-to-be-measured introduction section 60 and an $NO_x$ detecting section 70. In the gas-to-be-measured introduction section 60, a gas intake 63 and a gas exhaust port 64 are formed on the tip side of a cylindrical probe 62. Lattices 65 and 66 are disposed on the gas intake 63 and the gas exhaust port 64 at given intervals, respectively. Within the probe 62, an inner tube 67 having a flange 67a is concentric with the probe 62. Then, as indicated by an arrow in the figure, the gas to be measured which is taken in from the gas intake 63 enters the interior of the inner tube 67, returns to a space between the inner tube 67 and the probe 62 at an end portion of the inner tube 67, and is then exhausted to the exterior of the probe 62 from the gas exhaust port 64.

A $NO_x$ detecting section 70 is so structured that a $NO_x$ sensor unit 73 is received within a detecting section body 72. The $NO_x$ sensor unit 73 is provided with a plate-like $NO_x$ sensor 74 so that the sensor 74 is exposed to one end of the sensor unit 73, and is also integrated with a terminal block 75 used to electrically connect the $NO_x$ sensor 74 to the external through screwing means or the like, on the other end of the sensor unit 73. The outer peripheral portion of the end of the detecting section body 72 is provided with a flange 77 for connecting the gas-to-be-measured introduction section 60 to the $NO_x$ detecting unit 70.

In the middle portion of the detecting section body 72 is disposed a calibrated gas intake 78 for supplying a calibrated gas to the $NO_x$ sensor 74. Also, on an end portion opposite to the end portion of the detecting section body 74 where the sensor 74 is disposed, there is provided a flange 79 and a cap 80 for receiving the terminal block 75 therein. On a side surface of the flange 79 is defined a wiring port 81 for leading out an electrode from the terminal block 75 (wiring of the drive section, etc., which will be described later) etc., to the external. In the $NO_x$ sensor unit 73, a gas seal portion using an O ring 82 is disposed to prevent the gas to be measured from leaking to the terminal block 75. It should be noted that a terminal screw 86 for fixing the terminal block 75 and the $NO_x$ sensor unit 73 to the $NO_x$ detecting section 70 is fitted to the terminal block 75.

The terminal block 75 is provided with a drive section 85 including an amplifier, and the drive section 85 is electrically connected to a receiver 90 including an operating section, an display output section, and so on to conduct the pumping action of the $NO_x$ sensor 74, a predetermined arithmetic operation, and display/output.

In the above manner, the drive section is integrally structured in the vicinity of the gas sensor, and the pumping current in the drive section is amplified by the amplifier and then led to the operating section, thereby being capable of reducing an electrical noise.

Also, in the gas analyzer according to the present invention, it is preferable that the pumping currents (Ip3) to plural known amounts of the gas component to be measured are measured to prepare calibration curves to thereby calibrate the present gas analyzer. In other words, data relating to the pumping currents (Ip3) to the plural known amounts of the gas component to be measured are stored in the operating section of the gas analyzer, and on the basis of that data, the pumping current (Ip3) of the gas component to be measured in question is converted or calibrated to the amount of the gas component to be measured.

Figure 7:
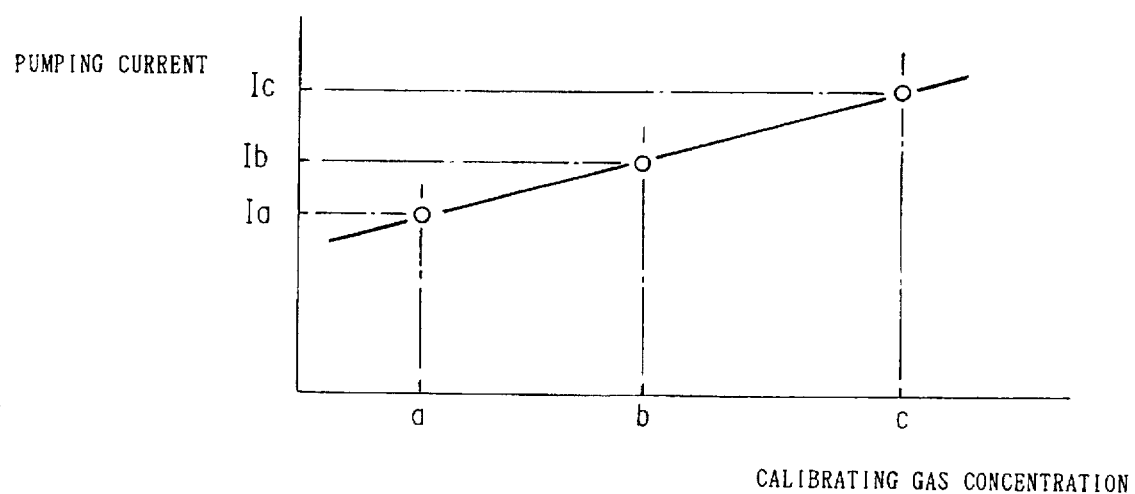
FIG. 7 is a graph showing a calibration curve.

For example, as shown in FIG. 7, measurement is made using the calibrated gas (standard gas) of the respective concentrations a, b and c, the pumping current (1a, 1b, 1c) at that time are obtained, respectively, to obtain the calibration curves. The calibration curve is a line, a multi-order curve, or the like, and the calibration curve can be automatically prepared in the operating section.

It is more preferable that the aforementioned oxygen reliability or equivalent reliability is measured so as to adjust the calibration curve.

It is preferable that the gas analyzer according to the present invention is calibrated using the calibration curve as described above. It is preferable to use a gas containing at least any one kind of gas component selected from $H_2O$ and $CO_2$ in addition to the known gas component to be measured as the known gas component to be measured (calibrated gas) used at that time.

Figure 8:
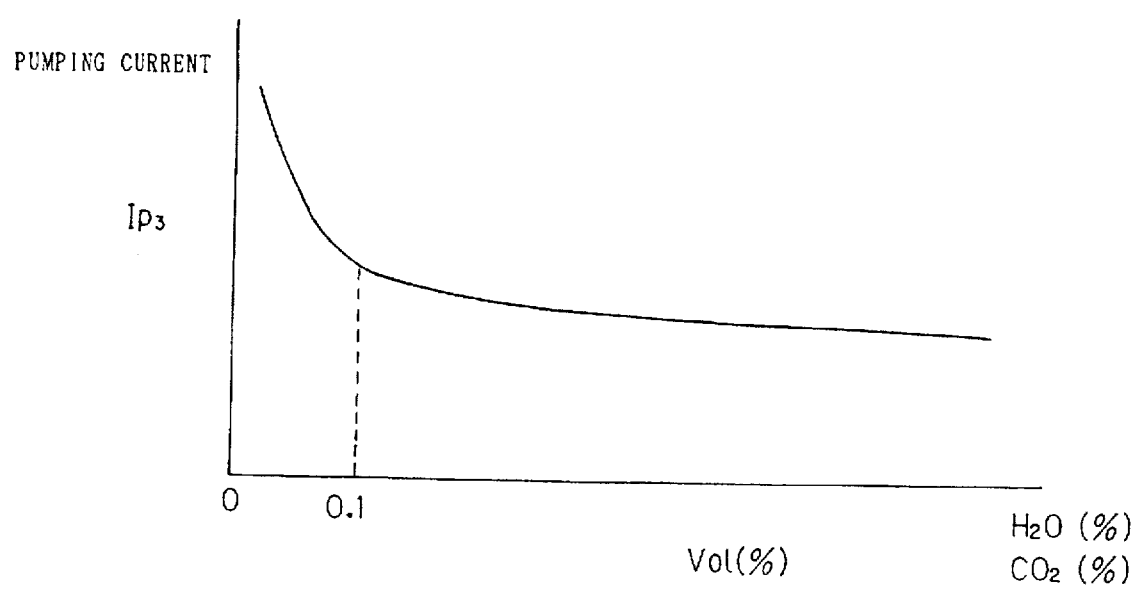
FIG. 8 is a graph showing a relationship between the content of $H_2O$ and $CO_2$ in a calibrated gas and the pumping current (lp3).

In other words, as shown in FIG. 8, if a calibrated gas that does not contain $H_2O$ or $CO_2$ is used, the generated electromotive force of the solid electrolyte is lowered so that the pumping current (Ip3) is increased, and sometimes unstabilized, to thereby lower the reliability of a numeral value of the concentration of gas to be measured. On the other hand, if a calibrated gas that contains at least any one kind of gas component selected from $H_2O$ and $CO_2$ is used, the pumping current (Ip3) is stabilized. Although the reason is not found, it is presumed that this is caused by a change or the stabilization of the surface state of the electrode of the solid electrolyte.

The added amount of $H_2O$ and $CO_2$ is preferably 0.1 vol% or more, respectively or in total, and more preferably 1 vol% or more.

In the gas analyzer according to the present invention, there is a case in which CO, OH or a poisoning material is excessively adsorbed on the electrode of the solid electrolyte that constitutes the electro-chemical pump cell in a predetermined period before or after its use, to thereby lower an accuracy in analysis of the gas analyzer.

For that reason, it is preferable that in the gas analyzer, the poisoning material or the like is separated from the electrode of the solid electrolyte before measuring the calibration curve, and the gas analyzer is calibrated in a normal state of the electrode.

The separating method is roughly classified into a method of increasing the temperature of the sensor and a method of forcedly supplying electricity.

In other words, there is preferably used a method in which after the temperature of the sensor having the electro-chemical pump cell is increased 50° C. higher than its working temperature for a given period, it returns to the working temperature to prepare the calibration curve of the calibrated gas (method of increasing the temperature of the sensor). In this method, a period during which the sensor is held to a high temperature is satisfactorily about 10 minutes.

Also, as the method of forcedly applying electricity, there is preferably used a method in which the sensor is separated from the drive section, and an alternating current power supply is connected between the respective electrode pair in the first to third processing zones, and after an alternating current of, for example, 1 Hz or higher flows for a given period, the sensor is returned to a drive state to prepare the calibration curve of the calibrated gas. In this method, a period during which the alternating current flows is satisfactorily about 10 minutes.

As was mentioned above, the present invention was described in detail, it is needless to say that the present invention can be embodied in the modes which have been subjected to a variety of alterations, corrections, improvements and so on, and also it should be understood that the modes of the embodiment belong to the scope of the present invention so far as they depart from the subject matter of the present invention.

As was described above, according to the gas analyzer and the method of calibrating the gas analyzer of the present invention, the stabilized pumping current and electromotive force corresponding to the concentration of the gas to be measured such as $NO_x$ in question can be obtained, and the concentration of the gas component to be measured can be accurately measured. Also, even though the concentration of oxygen in the gas to be measured is high, measurement is enabled without being adversely affected by the high concentration, with an excellent continuous response and with an accuracy for a long time, and a high S/N ratio can be obtained in the measurement of the gas component to be measured with a low concentration, to thereby obtain a large change in signals.

The foregoing description of a preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A gas analyzer comprising:

a gas sensor in which after a gas to be measured containing a gas component to be measured having bound oxygen to be measured is introduced into a first processing zone under a predetermined diffusion resistance, and an oxygen partial pressure in the atmosphere within said first processing zone is controlled to a predetermined oxygen partial pressure due to the pumping action of oxygen by the first electro-chemical pump cell in said first processing zone, the gas to be measured is introduced into a second processing zone under a predetermined diffusion resistance, and oxygen is pumped out by the second electro-chemical pump cell in the second processing zone, so that the oxygen partial pressure in said atmosphere is controlled to a low oxygen partial pressure value that does not substantially influence the measurement of the amount of the gas component to be measured, and thereafter the gas to be measured is introduced into a third processing zone, and said gas component to be measured in the atmosphere introduced from said second processing zone is reduced or decomposed in said third processing zone, and oxygen generated at that time is pumped out by a third electro-chemical pump cell to detect a pumping current flowing in said third electro-chemical pump cell;

a drive section for pumping oxygen from said first to third processing zones in said gas sensor;

an operating section for operating the pumping current flowing in said third electro-chemical pump cell into a value of the gas to be measured;

a display output section for displaying the value operated by said operating section, or outputting the value to an external as an electric output; and a heater drive section for heating said gas sensor to a predetermined temperature.

2. A gas analyzer as claimed in claim 1, wherein the gas component to be measured is $NO_x$.

3. A gas analyzer as claimed in claim 2, wherein the pumping current in the first processing zone and the pumping current in the second processing zone are introduced into said operating section, and said operating section operates the pumping currents in the first and second processing zones to output the amount of oxygen, the amount of insufficient oxygen or its equivalent in the atmosphere to be measured.

4. A gas analyzer as claimed in claim 3, wherein the measured $NO_x$ is corrected according to the amount value of oxygen, the amount value of insufficient oxygen or an equivalent value of oxygen in the atmosphere to be measured.

5. A gas analyzer as claimed in claim 1, wherein the pumping current in the first processing zone and the pumping current in the second processing zone are introduced into said operating section, and said operating section operates the pumping currents in the first and second processing zones to output the amount of oxygen, the amount of insufficient oxygen or its equivalent in the atmosphere to be measured.

6. A gas analyzer as claimed in claim 1, wherein at least said drive section is integrated with said gas sensor.

7. A method of calibrating a gas analyzer which includes a gas sensor in which after a gas to be measured containing a gas component to be measured having bound oxygen to be measured is introduced into a first processing zone under a predetermined diffusion resistance, and an oxygen partial pressure in the atmosphere within said first processing zone is controlled to a predetermined oxygen partial pressure due to the pumping action of oxygen by the first electro-chemical pump cell in said first processing zone, the gas to be measured is introduced into a second processing zone under a predetermined diffusion resistance, and oxygen is pumped out by the second electro-chemical pump cell in the second processing zone, so that the oxygen partial pressure in said atmosphere is controlled to a low oxygen partial pressure value that does not substantially influence the measurement of the amount of the gas component to be measured, and thereafter the gas to be measured is introduced into a third processing zone, and said gas component to be measured in the atmosphere introduced from said second processing zone is reduced or decomposed in said third processing zone, and oxygen generated at that time is pumped out by a third electro-chemical pump cell to detect a pumping current flowing in said third electro-chemical pump cell; said method comprising the step of:

calibrating said gas analyzer with a plurality of known gas component to be measured as a standard gas and a pumping current corresponding to the standard gas as a calibration curve.

8. A method of calibrating a gas analyzer as claimed in claim 7, wherein a standard gas containing at least $H_2O$ and $CO_2$ is used as the known gas component to be measured other than the gas component to be measured.

9. A method of calibrating a gas analyzer as claimed in claim 8, wherein a temperature of said gas sensor is increased 50° C. higher than a working temperature for a predetermined time before measuring the calibration curve, and the temperature of said gas sensor is returned to the working temperature to prepare the calibration curve of the standard gas.

10. A method of calibrating a gas analyzer as claimed in claim 7, wherein a temperature of said gas sensor is increased 50° C. higher than a working temperature for a predetermined time before measuring the calibration curve, and the temperature of said gas sensor is returned to the working temperature to prepare the calibration curve of the standard gas.

11. A method of calibrating a gas analyzer as claimed in claim 7, wherein, before measuring the calibration curve, said gas sensor is separated from said drive section, and an alternating current power supply is connected between respective electrode pairs of said first to third processing zones, and after an alternating current of 1 Hz or higher is supplied for a predetermined time, said gas sensor is returned to a drive state to prepare the calibration curve of the standard gas.

* * * * *